United States Patent
Lee et al.

(10) Patent No.: US 8,679,539 B2
(45) Date of Patent: *Mar. 25, 2014

(54) DRUG-LOADED POLY (ALKYL-CYANOACRYLATE) NANOPARTICLES AND PROCESS FOR THE PREPARATION THEREOF

(75) Inventors: Yu-Der Lee, Hsinchu (TW); Chi-Yu Huang, Pingtung County (TW); Chih-Ming Chen, Kaohsiung County (TW)

(73) Assignee: Tong Shen Enterprise Co., Ltd., Linyuan Township, Kaohsiung County (TW)

( * ) Notice: Subject to any disclaimer, the term of this patent is extended or adjusted under 35 U.S.C. 154(b) by 1676 days.

This patent is subject to a terminal disclaimer.

(21) Appl. No.: 11/700,226

(22) Filed: Jan. 31, 2007

(65) Prior Publication Data

US 2008/0182776 A1 Jul. 31, 2008

(51) Int. Cl.
*A61K 9/14* (2006.01)

(52) U.S. Cl.
USPC ............................. 424/489; 424/501; 514/951

(58) Field of Classification Search
USPC .......................................................... 424/489
See application file for complete search history.

(56) References Cited

U.S. PATENT DOCUMENTS

| | | | | |
|---|---|---|---|---|
| 5,641,515 A | * | 6/1997 | Ramtoola | 424/489 |
| 6,881,421 B1 | * | 4/2005 | da Silveira et al. | 424/489 |
| 2001/0010824 A1 | * | 8/2001 | Handjani et al. | 424/401 |

OTHER PUBLICATIONS

Limouzin et al. Macromolecules 2003, 36, 667-674.*
Mitra et al. Journal of Pharmacy and Pharmacology, vol. 55, Issue 7, pp. 895-902, Jul. 2003.*

* cited by examiner

*Primary Examiner* — James Rogers
(74) *Attorney, Agent, or Firm* — Muncy, Geissler, Olds & Lowe, P.C.

(57) ABSTRACT

A process for preparing the drug-loaded cyanoacrylate nanoparticles is described. The cyanoacrylate nanoparticles which effectively deliver biological and therapeutic agents are synthesized by miniemulsion polymerization with surfactant, pluronic F127 or F68. Before initiation of polymerization, active agents with particularly highly hydrophobicity are dissolved in cyanoacrylate monomer. Compared with the drug-loaded polyalkylcyanoacrylate nanoparticles produced by emulsion polymerization, those produced by miniemulsion polymerization possess higher loading and encapsulation efficiencies. While the content of dissolved agents increases, furthermore, the loading and encapsulation efficiencies increase concurrently.

1 Claim, 4 Drawing Sheets

DRUG-LOADED POLY (ALKYL-CYANOACRYLATE) NANOPARTICLES AND PROCESS FOR THE PREPARATION THEREOF

FIELD OF THE INVENTION

The present invention relates to a process for preparing nanoparticles. More particularly, the invention relates to a process for preparation of nanoparticles for drug delivery.

BACKGROUND OF THE INVENTION

To obtain more efficient medication, multiple biodegradable materials were developed for drug delivery carrier, such as poly(lactic acid) (PLA), poly(glycolic acid) (PGA), poly (lactid-co-glycolide) (PLGA) and poly(alkyl-cyanoacrylate) (PACA). Therapeutic agents, particularly anti-cancer drugs, might undergo degradation gradually or cause systemic side effects through intravenous injection or oral administration. Patients not only seriously suffered but also received insufficient therapeutic drugs. While encapsulated in the nanoparticles, these drugs were fully protected by polymers and possessed high stabilities in the in vivo and in vitro studies. In addition, by modulating compositions of the nanoparticles, the drug-loaded particles might be delivered to target cells or tissues and achieve the specificity of treatment. Therefore, biodegradable nanoparticles were used extensively.

Biodegradable PACA had developed as an effective drug delivery device for sustained and localized administration of various pharmacologically active agents, such as cytotoxic drugs, antibiotics, peptides, and genes. For therapeutic use, the drug-loading efficiency of nanoparticles must be maximized in order to minimize the amount of carrier. According to the previous studies, PACA nanoparticles with porous structure possessed a highly specific area on which various quantities of agents were adsorbed. The formed nanoparticles obtained the capability of encapsulating a wide range of drugs, and their non-solvent clear manufacturing process allowed them as the effective drug delivery device.

Conventional techniques for preparing drug-loaded PACA nanoparticles were by anion emulsion polymerization process in surfactant-containing acidic aqueous solution. The capsulated drugs, dissolved in the medium during or after polymerization, were stable reserved in the nanoparticles. However, the delivery system composed of PACA had low loading efficiency for poorly water-soluble drugs. There were several strategies used to increase the carrier capacity, such as selection of stabilizer, adjustment of pH of the medium, the amount and time of drug addition or modulating hydrophilic/ hydrophobic properties of polyalkylcyanoacrylate. However, the maximum weight of the entrapped drug was limited to that dissolved in the medium.

Paclitaxel was a quite effective chemotherapeutic agent and had been clinically applied to treat a wide range of tumors, such as ovarian cancer, breast cancer, bladder cancer, esophagus cancer, melanoma and leukemia. Paclitaxel was used, in general, in the form of self-emulsifying system due to its fairly low water solubility (less than 3 ng/ml). Therefore, the solubilization technique of this drug had been developed along with the drug itself, particularly for systemic administration. The solubilization technique was the use of solubilizing agents, such as Cremophore EL (polyethoxyethylene 35 castor oil), polyoxyethoxylated castor oil and dehydrated alcohol. Before clinical administration, paclitaxel dissolved in solubilizing agents was dispersed in excess amount of normal saline or dextrose solution (5%). However, these solubilizing agents had serious toxic side effects. Cremophore EL, for instance, caused hypersensitivity, neurotoxicity, enphorotoxicity and cardiotoxicity. In present studies, biodegradable polymeric micro/nanoparticles, liposomes, core/ shell nanoparticles, micelles or dendritic polymers were utilized for the construction of paclitaxel-loaded nanoparticles.

As described above, the drug-delivery nanoparticles composed of PACA encapsulated hydrophobic agents with low loading efficiency. In the preparation process of the therapeutic nanoparticles by conventional emulsion polymerization, drugs were dissolved in the polymerization medium before introducing monomer or added after the polymerization so that drugs were encapsulated during polymerization or adsorbed in the particles. Hence, the solubility of drug in the polymerization medium decided the amount of drug encapsulation. It seemed impracticable to obtain paclitaxel-loaded PACA nanoparticles with high loading efficiency by conventional emulsion polymerization, due to the low water solubility of paclitaxel. Furthermore, in conventional emulsion polymerization, the active molecules were transported slowly or sparsely through the water phase and onto the growing reaction sites, especially for those highly hydrophobic agents. Eventually, it would result in large amount of precipitate and aggregate. The produced nanoparticles were not only with low encapsulation efficiency of the encapsulants, while the waste of active agents was significant as well.

In view of the limitation of prior process of PACA emulsion polymerization, it would be desirable to produce nanoparticles with high stability and high loading/encapsulation efficiencies for hydrophobic agents. It would be desirable to preclude the reaction materials from further wasting.

SUMMARY OF THE INVENTION

The present invention provides a process for preparing drug-loaded poly(alkyl-cyanoacrylate) nanoparticles with high loading and encapsulation efficiencies. Particularly for the highly hydrophobic agents, the solubility of encapsulants in polymerization medium critically determines the drug-loading efficiency of carrier. In order to increase the loading and encapsulation efficiencies of PACA nanoparticles, miniemulsion polymerization process is utilized consequently. Miniemulsion polymerization process is typically preformed by subjecting a system of monomer, water, surfactant and a highly water insoluble compound, so-called hydrophobe, to high shear fields. Miniemulsion droplets are of different sizes and of stable dispersion.

In the present invention, comparing with nanoparticles prepared by emulsion polymerization, poly(n-butyl cyanoacrylate) (PBCA) nanoparticles prepared by miniemulsion polymerization process are higher loading and encapsulation efficiencies for hydrophobic monomers, such as paclitaxel and flutamide. While the contents of these hydrophobic monomers are increased, the loading and encapsulation efficiencies of the nanoparticles increase concurrently. The paclitaxel encapsulated in PBCA nanoparticles is distributed either molecularly in the polymers, in an amorphous state, or in a crystalline state with crystal size too small to be detected. Therefore, miniemulsion polymerization is feasible for preparing drug-load poly(alkyl cyanoactylte) nanoparticles, such as PBCA.

DETAILED DESCRIPTION OF THE PREFERRED EMBODIMENTS

Figure 1:
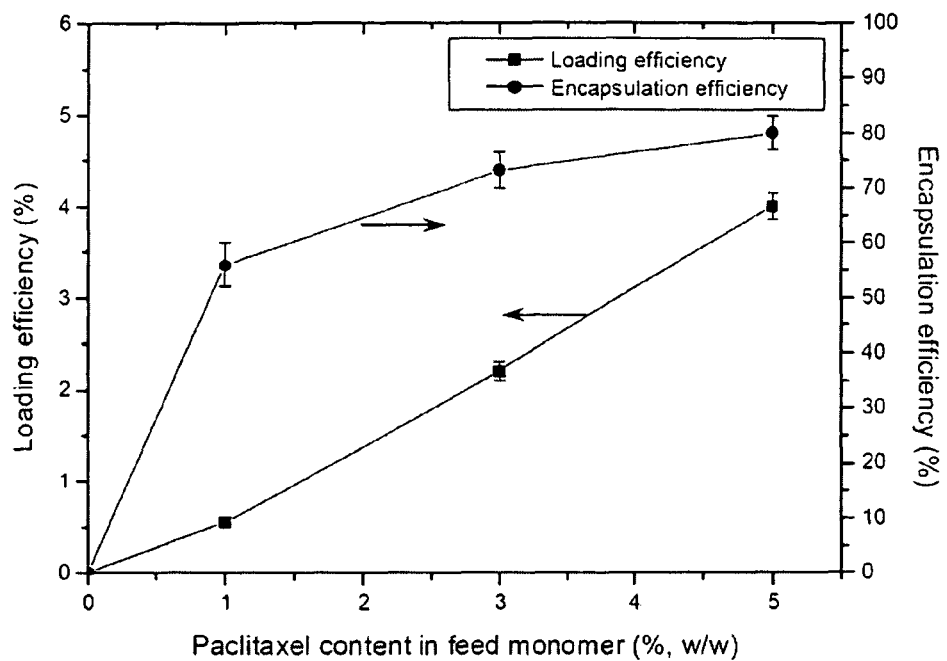
FIG. 1. The influence of paclitaxel content in feed monomer on loading efficiency (L.E.) and encapsulation efficiency (E.E.) of paclitaxel-loaded PBCA nanoparticles FIG. 2. FE-SEM [SE(M)] picture of paclitaxel-loaded PBCA nanoparticles with 4.0% L.E. prepared by miniemulsion polymerization process FIG. 3. X-ray powder diffraction patterns of: (a) paclitaxel, (b) PBCA nanoparticles, (c) paclitaxel-loaded PBCA nanoparticles prepared by emulsion polymerization process, (d) paclitaxel-loaded PBCA nanoparticles prepared by miniemulsion polymerization process, (e) paclitaxel-loaded PBCA nanoparticles with 2.2% L.E. prepared by miniemulsion polymerization process, and (f) paclitaxel-loaded PBCA nanoparticles with 4.0% L.E. prepared by miniemulsion polymerization process.

The present invention provides a process for preparing high loading and encapsulation poly(alkyl cyanoacrylate) nanoparticles for biological and therapeutic agents. More particularly, the nanoparticles formed by this process are feasible to load highly hydrophobic drugs.

The following instance of the process for the synthesis of drug-loaded cyanoacrylate nanoparticles is illustrative, but not limiting the scope of the present invention. Reasonable variations, such as those occur to reasonable artisan, can be made herein without departing from the scope of the present invention.

The paclitaxel-loaded PBCA nanoparticles were prepared by miniemulsion and emulsion polymerization processes, respectively. Since BCA is an extremely active monomer, even the presence of a weak basic substance is capable of initiating the anionic polymerization. For obtaining a stable a stable solution of monomer containing paclitaxel, it is required for BCA having high purity and containing little inhibitor of $SO_2$. And the detailed methods were described as below:

Paclitaxel was dissolved in n-butyl cyanoacrylate (BCA) with the aid of mild heating (60° C.) and sonication. For all experiments, 0.5 g of the paclitaxel containing monomer or non-containing BCA monomer was added at once to a 50 ml aqueous solution of a initiator, 0.01N hydrochloric acid, containing surfactant pluronic F127 [poly(ethylene oxide)-poly(propylene oxide)-poly(ethylene oxide)triblock copolymer].

During miniemulsion polymerization process, the aqueous solution and the paclitaxel containing monomer were mixed using a magnetic stirrer at high speed (~1,000 rpm) for five minutes at room temperature (~20° C.) to yield a pre-emulsion. The pre-emulsion was sonicated for 60 seconds in an ice bath with an energy output of 110 W using a Branson Sonifier (Model 450) and then gently stirred at 250 rpm for further 3 hours. Paclitaxel containing monomers with various paclitaxel concentrations (0%, 1%, 3%, and 5% (w/v)) were used to produce drug-loaded nanoparticles with constant 0.5% (w/v) of pluronic F127 in order to investigate the effects of drug concentrations on drug loading and encapsulation efficiencies.

While in the emulsion process, the paclitaxel containing monomer of 1% (w/w) was dispersed in the aqueous solution containing 0.5% (w/v) of pluronic F127 and polymerized with high-speed stirring for 4 hours at room temperature.

The resulting dispersions were filtered through a 1.0 μm filter to eliminate non-incorporated drugs and aggregated particles. Formed drug-loaded nanoparticles were separated by ultracentrifugation at 100,000×g for 60 minutes (CP 100MX, Hitachi, Japan) at 4° C. and dispersed again in water and lyophilized for three days.

The prepared nanoparticles by miniemulsion and emulsion polymerization processes were respectively examined for several characteristics, including particle size, size distribution, particle surface charge and drug loading and encapsulation efficiencies.

The particle size and size distribution of drug-loaded PBCA nanoparticles were elucidated by photon correlation spectroscopy (PCS; Zetasizer 3000, Malvern Instruments, Malvern, UK) at 25° C. Scattered light with a wavelength of 633 nm was detected at an angle of 90°. The dispersion was diluted with deionized water to a favorable concentration for better measurement. The average size of hydrodynamic particle was expressed as the value of z-average size ±S.D. from three replicate samples. The width of the size distribution was indicated by the polydispersity index (P.I.).

The particle surface charge was analyzed as followed. Drug-loaded and unloaded PBCA nanoparticles suspensions were diluted with deionized water to ensure that the signal intensity was suitable for the instrument. The zeta potential was measured by laser Doppler velocimetry (Zetasizer 3000, Malvern Instruments, Malvern, UK) at 25° C. Values were presented as mean±S.D. from three replicate samples.

The method for determining the paclitaxel loading and encapsulation efficiencies of PBCA nanoparticles was, according the previous worker (Ruan, G., Feng, S. S., 2003. Biomaterials, 24, 5037-5044). 6 mg of lyophilized nanoparticles were dissolved in 1 ml dichloromethane (DCM), and 6 ml acetonitrile/water (50/50, v/v) was then added and stirred under dry nitrogen stream to evaporate DCM at room temperature, and thus the paclitaxel payload in nanoparticles was determined. The resulting solution was filtered through 0.45 μm polytetrafluoroethylene (PTFE) membrane filters. 20 μl of the filtered solution was injected into a high performance liquid chromatographic (HPLC) apparatus. The HPLC apparatus was equipped with a Waters 510 solvent delivery pump, a luna C18 (2) column (5 μm, 250 mm×4.6 mm, Phenomenex, USA) and a UV/VIS detector (Laballiance, USA), operating at a wavelength of 227 nm. The mobile phase was acetonitrile/water (50/50, v/v) and the flow rate was 1.0 ml/min. The concentration of drug in the solution was obtained from the calibration curve, which related peak areas and concentrations. The curve was linear in the range of 50-50,000 ng/ml with a correlation coefficient of $R^2=1.0$. Results were expressed as the means of three measurements.

The recovery efficiency of this extraction procedure was examined using paclitaxel with known weight: 0.03 to 0.3 mg, mixed with 6 mg of drug-free PBCA nanoparticles, and the procedure of extraction, described previously, was repeated. All the recoveries were approximately 95%, which revealed that approximate 95% of the original paclitaxel could be extracted by this procedure from the mixture of paclitaxel and PBCA nanoparticles. The loading efficiencies of paclitaxel in PBCA nanoparticles determined by this procedure of extraction were corrected accordingly. The drug loading efficiency (L.D.) and drug encapsulation efficiency (E.E.) were defined as follows.

$$\text{Drug loading efficiency (\%, w/w)} = \frac{\text{mass of drug in nanoparticles}}{\text{mass of nanoparticles}} \times 100$$

$$\text{Drug encapsulation efficiency (\%, w/w)} \equiv \frac{\text{mass of drug in nanoparticles}}{\text{mass of feed drug}} \times 100$$

The characteristics of paclitaxel-loaded PBCA nanoparticles produced by miniemulsion or emulsion polymerization process were described in Table 1 below.

TABLE 1

| Method | Emulsion[a] | Miniemulsion[a] |
|---|---|---|
| Average diameter ± S.D. (nm) | 56.2 ± 2.0 | 99.7 ± 4.4 |
| Polydispersity index (P.I.) | 0.132 | 0.248 |
| Zeta potential ± S.D (mV) | −0.3 ± 0.3 | −19.3 ± 2.2 |
| Loading efficiency. ± S.D (%) | 0.18 ± 0.02 | 0.56 ± 0.04 |
| Encapsulation efficiency ± S.D (%) | 18.0 ± 2.0 | 56.6 ± 4.0 |

[a]Feed of monomer containing 1% (w/w) paclitaxel; surfactant pluronic F127 concentration, 0.5 g/ml.

Nanoparticles prepared by miniemulsion polymerization process were larger in particle size and had a wider size distribution than those produced by emulsion polymerization process. In addition, the loading and encapsulation efficiencies of the miniemulsion nanoparticles were higher. These results revealed that miniemulsion polymerization process was an effective method for encapsulating paclitaxel in PBCA nanoparticles. Zeta potential was the electrostatic potential of particle surface generated by ions accumulation. And it was a significant index to evaluate the stability of the particles. Lower zeta potential of PBCA nanoparticles produced by miniemulsion polymerization process (−19.3±2.2) represented for greater amount of surfactant cover on the surface of the particles. The particle size of the nanoparticles synthesized by miniemulsion polymerization process (99.7±4.4), hence, was obviously larger than those synthesized by emulsion process (56.2±2.0).

To analyze various contents of paclitaxel in nanoparticles, the feed BCA monomer with paclitaxel contents as, 0%, 1%, 3% and 5% (w/w), was added respectively in miniemulsion polymerization process which was described above. The produced PBCA nanoparticles were followed to analyze the loading and encapsulation efficiencies for paclitaxel (FIG. 1). While the contents of paclitaxel increased, the loading efficiency and the encapsulation efficiency were increased. A loading efficiency of over 4% (w/w) and an encapsulation efficiency of 80% (w/w) were achieved simultaneously when the drug content in the feed monomer was 5% (w/w).

Figure 2:
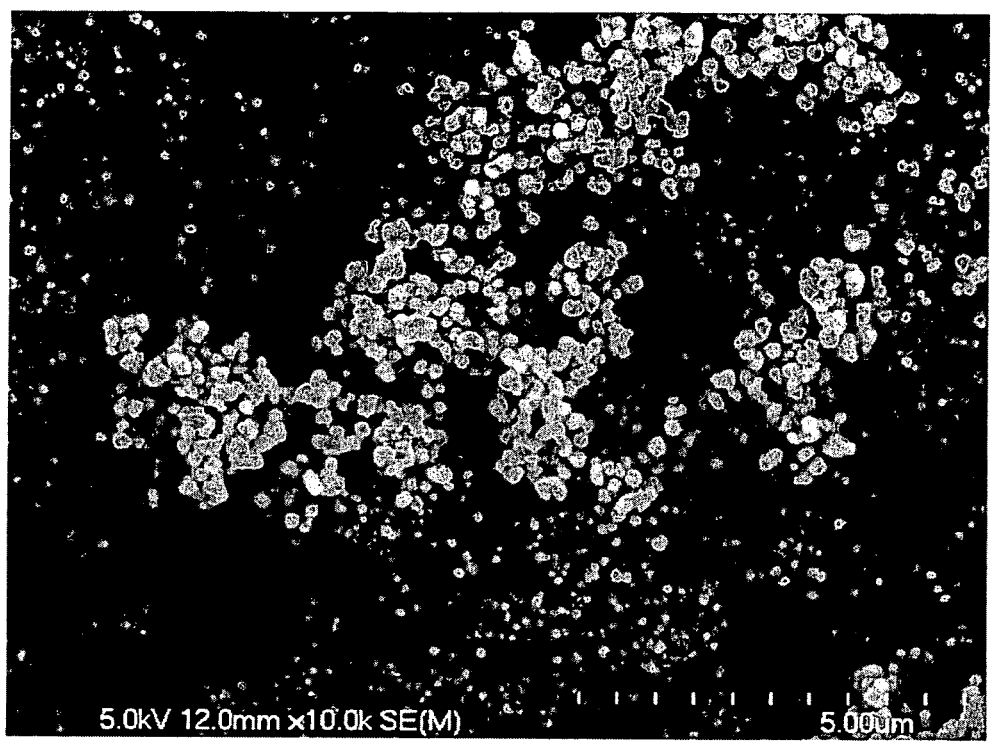

The collected products of paclitaxel-loaded PBCA nanoparticles with 4.0% loading efficiency (L.E.) were observed by field emission scanning electron microscopy (FE-SEM; Hitachi S-4700, Japan). Samples of collected products were placed on a 400 mesh carbon coated with cooper grid. After drying, the samples were observed at 15 kV. The prepared paclitaxel-loaded PBCA nanoparticles were of spherical shape with narrow distribution and did not show any aggregation (FIG. 2).

Figure 3:
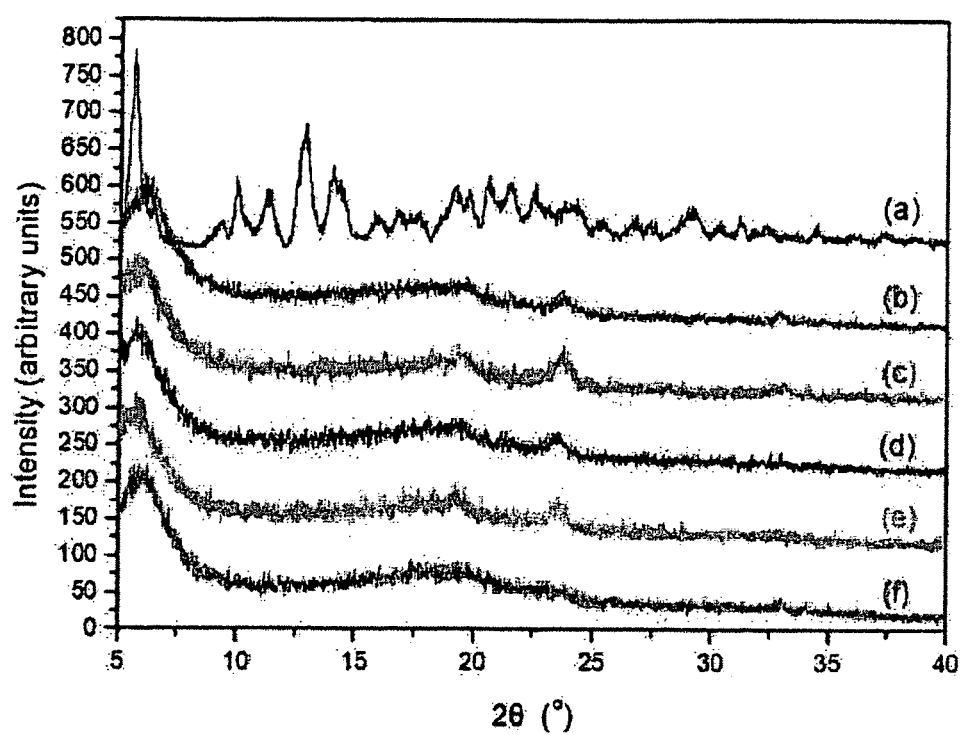

To confirm the morphology of paclitaxel in drug-loaded PBCA nanoparticles, PBCA nanoparticles and paclitaxel-loaded PBCA nanoparticles prepared by emulsion and miniemulsion polymerization processes with various drug loading efficiencies from 0.56% (w/w) to 4% (w/w) were examined by the X-ray powder diffraction (XRD). XRD spectra of paclitaxel poser, PBCA nanoparticles and paclitaxel-loaded PBCA nanoparticles were obtained using a XDS 2000 diffractometer (Scintag, USA) with Seifert ID 3000 software. The scanning range of 2θ was from 5° to 40° and the scanning rate was 1° 2θ/min with a step width of 0.02°. The X-ray source was CuK radiation (40 kV, 35 mA). The results were showed in FIG. 3.

According to the XRD data, paclitaxel-loaded PBCA nanoparticles showed no obvious signal, while paclitaxel exhibited several intense peaks at 2θ=5.6°, 9.9° and 12.7°. These peaks of paclitaxel, however, were not present in the XRD patterns of paclitaxel-loaded PBCA nanoparticles. The intensity of XRD peak depended on the crystal size. Therefore, the XRD data indicated that the paclitaxel loaded in PBCA nanoparticles would be either molecularly dispersed in the polymers, distributed in an amorphous state, or crystal with very small size.

The in vitro release profiles of paclitaxel from paclitaxel-loaded PBCA nanoparticles prepared by emulsion and miniemulsion polymerization processes were analyzed as below. Two milligrams of lyophilized drug-loaded nanoparticles were redispersed in 10 ml of phosphate buffer solution (PBS, pH 7.4 containing 0.1% w/v Tween 80) in a capped centrifuge tube. The tube was placed in a shaking incubator (120 rpm) at 37° C. Tween 80 was used to increase the solubility of paclitaxel in the release medium and to reduce the association of the drug with the container surface. At predetermined time, the tube was centrifuged at 39,000×g for 20 minutes. The collected particles were redispersed in 10 ml fresh PBS, containing Tween 80, for continuous release studies. The release of paclitaxel in the supernatant was extracted with 2 ml DCM and then 1 ml of acetonitrile/water (50/50, v/v) was added to the extract. After DCM was evaporated by a dry nitrogen stream, the drug concentration in the clear solution was analyzed by HPLC under the same analytic conditions as describe above.

Figure 4:
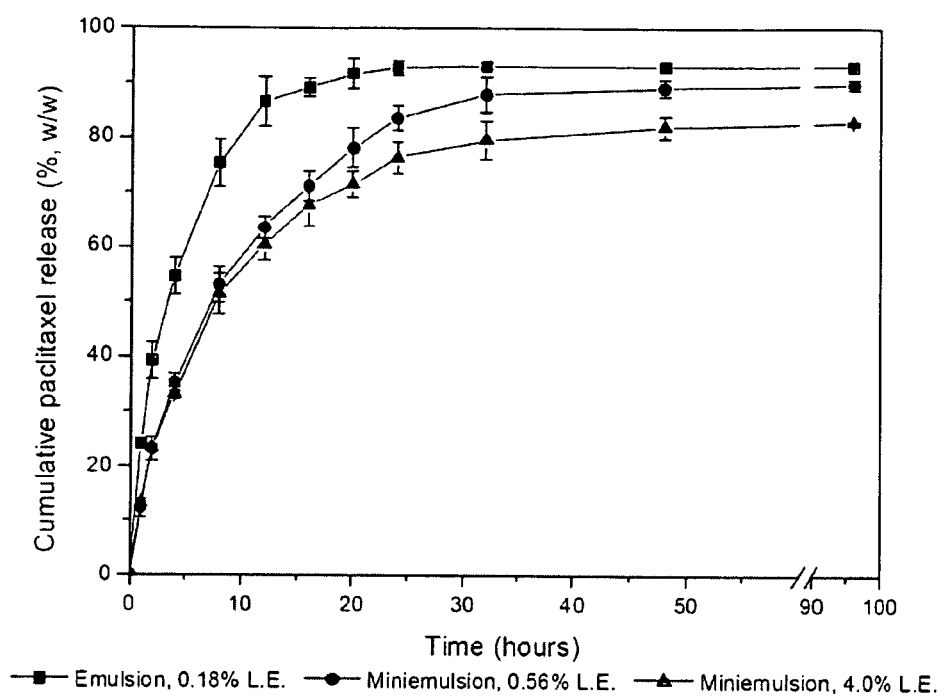
FIG. 4. In vitro cumulative paclitaxel release (mean±S.D., n=3) profile for paclitaxel-loaded PBCA nanoparticles prepared by emulsion polymerization process with drug-loading efficiency of 0.18% (w/w) and miniemulsion polymerization process with drug-loading efficiencies of 0.56% and 4% (w/w).

The in vitro release profiles were illustrated in FIG. 4. Paclitaxel-loaded PBCA nanoparticles prepared by emulsion polymerization process exhibited an initial rapid release to 85.6% (w/w) during the first 10 hours, followed by a slow release to 93.2% (w/w) until 96 hours. However, the percentage of drug released for paclitaxel-loaded PBCA nanoparticles after 96 hours were 89.7% and 82.9% (w/w) with loading efficiency of 0.56% and 4% (w/w), respectively. The release profile for paclitaxel-loaded PBCA nanoparticles produced by the emulsion polymerization process was rapid at first phase and followed by a slow release phase. It indicated that the encapsulated drugs were released virtually before the first 10 hours. Compared with emulsion polymerization process, however, paclitaxel-loaded PBCA nanoparticles prepared by miniemulsion polymerization process showed less burst effect and slower release profiles which might indicate a larger fraction of paclitaxel distributed in the nanoparticles. If the paclitaxel-loaded PBCA nanoparticles were applied for anti-cancer administration, the nanoparticles prepared by miniemulsion polymerization process were more feasible for sustained treatment than emulsion polymerization process.

In another embodiment, flutamide-loaded PBCA nanoparticles were produced by miniemulsion polymerization process as paclitaxel-loaded PBCA nanoparticles, but the surfactant pluronic F127 was replaced to pluronic F68. Flutamide is a hydrophobic anti-cancer drug as well and is applied to the treatment of hyperplasia and cancer of the prostate. To analyze the loading and encapsulation efficiencies of flutamide concentration in PBCA nanoparticles, the flutamide content in feed BCA monomer was varied as, 0%, 5% and 10%, with 0.5% (w/v) of pluronic F68 in miniemulsion polymerization process described above. The produced flutamide-loaded PBCA nanoparticles were collected and analyzed in loading and encapsulation efficiencies which processes were described above as well. The results were presented in Table 2.

TABLE 2

|  | Flutamide content (%, w/w) | | |
| --- | --- | --- | --- |
|  | 0 | 5 | 10 |
| Loading efficiency. ± S.D (%) | 0 | 4.2 | 9.9 |
| Encapsulation efficiency ± S.D (%) | 0 | 84.5 | 98.9 |

Loading and encapsulation efficiencies of flutamide-loaded PBCA nanoparticles were raised simultaneously with increase of flutamide concentration. These results were similar to the loading and encapsulation efficiencies of the hydrophobic drug, paclitaxel, encapsulated in PBCA nanoparticles produced by miniemulsion polymerization process. Therefore, miniemulsion polymerization process is a feasible method for preparing drug-loaded PBCA nanoparticles which are applied to deliver highly hydrophobic drugs, such as paclitaxel or flutamide.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

What is claimed is:

1. A method for preparing drug-loaded poly(n-butyl-cyanoacrylate) nanoparticles, the method comprising the steps of:
    forming a solution by dissolving a hydrophobic active agent in a poly(n-butyl-cyanoacrylate) medium while applying heating and sonication;
    adding an aqueous surfactant solution to the solution while stirring to yield a pre-emulsion; and
    sonicating the pre-emulsion followed by stirring to form the drug-loaded poly(n-butyl-cyanoacrylate) nanoparticles, wherein the hydrophobic active agent is paclitaxel or flutamide.

* * * * *